United States Patent [19]

Chin et al.

[11] Patent Number: 4,526,175
[45] Date of Patent: Jul. 2, 1985

[54] DOUBLE LUMEN DILATATION CATHETER

[75] Inventors: Albert K. Chin, San Francisco; Thomas B. Kinney, Mountain View, both of Calif.

[73] Assignee: Thomas J. Fogarty, Palo Alto, Calif.

[21] Appl. No.: 468,203

[22] Filed: Feb. 22, 1983

[51] Int. Cl.³ .............................................. A61M 29/02
[52] U.S. Cl. ..................................... 128/344; 604/98; 604/271
[58] Field of Search ........................... 128/344, 348.1; 604/96–103, 271

[56] References Cited

U.S. PATENT DOCUMENTS

| | | | |
|---|---|---|---|
| 3,168,092 | 2/1965 | Silverman | 128/344 X |
| 4,243,040 | 1/1981 | Beecher | 604/271 X |
| 4,271,839 | 6/1981 | Fogarty et al. | 128/344 |

Primary Examiner—Michael H. Thaler
Attorney, Agent, or Firm—Limbach, Limbach & Sutton

[57] ABSTRACT

A dilatation catheter is provided with an elongated balloon element having a distal evertable dilating portion and a proximal connector portion. The proximal connector portion extends through and past a large chamber where part of it may be layed-up in a loop or loops, and said connector portion also extends through O-ring braking and sealing structure.

3 Claims, 4 Drawing Figures

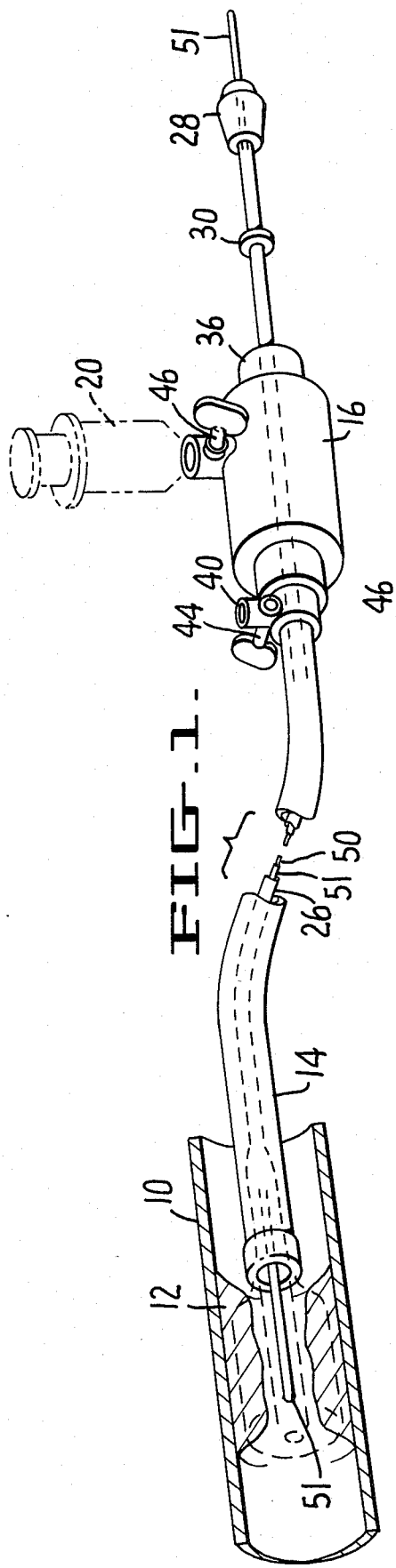

4,526,175

DOUBLE LUMEN DILATATION CATHETER

BACKGROUND OF THE INVENTION

(1) Field of the Invention

The invention relates to a dilatation catheter having an evertable balloon element which is attached to the distal end of the catheter and stored in inverted condition in the catheter. The improved catheter of the invention has an inner catheter which is connected to the evertable end of the balloon so as to define an always open, through lumen, enabling the catheter to be moved over a pre-placed guide wire to the arterial site for use.

(2) Description of the Prior Art

The closest prior art of which we are aware is the third embodiment (FIGS. 7-10) of Fogarty et al U.S. Pat. No. 4,271,839.

SUMMARY OF THE INVENTION

The catheter of the invention is provided with an inner catheter having at its distal end an inverted annular balloon. The proximal end of the inner catheter extends through a reservoir chamber and then through an O-ring seal which may be tightened as well as loosened. When the seal is loosened, the proximal end of the inner catheter may be fed forwardly into the reservoir chamber for loop formation and consequent storage or the proximal end of the inner catheter may be moved in the opposite direction through the O-ring to retract and reinvert the balloon. Tightening of the O-ring, after catheter loop formation in the reservoir chamber, conditions the catheter for balloon eversion and depletion of the loop or loops.

DESCRIPTION OF THE DRAWING

FIG. 1 is a view in perspective illustrating an occluded vessel and the catheter of the invention in proximity to the occlusion.

FIG. 2 is an enlarged view in diametral section of the catheter of FIG. 1 in a pre-eversion condition of operation.

FIG. 3 is a view taken along lines 3—3 of FIG. 2.

FIG. 4 is a view in diametral section of the catheter illustrating the condition of the balloon when it is being used to dilate an occlusion.

DESCRIPTION OF THE PREFERRED EMBODIMENT

FIG. 1 shows a blood vessel 10 partially occluded by occlusion 12.

The catheter comprises a catheter body 14, a catheter housing 16 to which the body 14 is fixedly connected, a balloon inflation port 18, a fluid syringe 20 in feed relation to port 18, and an annular, elongated balloon 22 having a dilating portion 24 and a connecting portion 26 which extends through the housing 16 and is attached to a fitting 28. The catheter body 14 constitutes an outer catheter and balloon portion 26 constitutes an inner catheter.

The catheter is provided with movement control means for the inner catheter 26 comprising stop ring 30 carried by the inner catheter 26, O-ring 32, and O-ring housing comprising an external threaded sleeve 34 carried by housing 16 and O-ring compression nut 36 in threaded engagement with sleeve 34.

The catheter is further provided with a purge lumen 37 defined within an inwardly directed rib-like portion 38 of outer catheter 14, syringe fitting 40 having a discharge port 42 in communication with lumen 36. Control valves 44 and 46 are provided in association with ports 42 and 18. A reservoir chamber 48 within housing 16 has a diameter which is preferably on the order of 5-10 times as great as the diameter of outer catheter 14.

A typical way of installing the catheter at the treatment site, as shown in FIG. 1, is to thread a guide wire 50 through the vessel 10 to the occlusion 12, thread a length of small catheter 51 onto wire 50 to protect the balloon 22 from wire 50, and to then move the catheter along the wire until it is positioned as shown in FIG. 1. The small catheter 51 and the wire 50 are then withdrawn, although the wire may be left in place. In the FIG. 1 emplacement condition of the catheter, the inner catheter 26 is in a pulled-straight condition and held in that condition by tightening the nut 36 to compress the O-ring and thereby move the latter into gripping relation with the inner catheter.

Once the catheter has been advanced into the desired position proximal to the stenosis to be dilated, the O-ring nut 36 is loosened to cause the O-ring 32 to move out of gripping relation with the inner catheter 26. The inner catheter is then fed inwardly of the housing 16 until the stop member 30 engages nut 36. With the wire 50 in place within the catheter, the inner catheter forms a take-up loop 42 within housing chamber 48. This take-up loop allows for subsequent full eversion of the dilating portion 24 of balloon 22. The nut 36 is then tightened to move the O-ring 32 into gripping sealing relation with the inner catheter.

A fluid medium is then infused via port 42 so that it totally fills the catheter and the reservoir chamber 48. This is done in order to purge the catheter of air and to fill it with the fluid medium which is subsequently used for balloon inflation. The purge port valve 44 is then closed, syringe 20 is attached to the housing 16, and the inflation port valve 46 is opened. The syringe 20 is then operated, as shown in FIG. 4, to evert the balloon 24, thereby depleting the storage loop 52 in chamber 48, and to thereafter inflate the balloon to dilate the occlusion 12. During eversion of the balloon, the loop of inner catheter stored in the housing unrolls in a manner to impart resistance to balloon eversion.

Thereafter, following removal of the fluid medium from the catheter, the balloon may be re-inverted by loosening the nut 36 and by then pulling the proximal end of the inner catheter to the position shown in FIG. 1.

The subject dilatation catheter provides a passageway from the proximal end of the catheter to the distal tip thereof. This passageway, the ends of which are indicated at 54 and 56 in FIG. 4, allows the catheter to be used with a guide wire in a manner in which angiographers are accustomed. That is, a guide wire and a simple catheter, not used for dilatation, are manipulated until the guide wire lies in the particular branch vessel to be dilated, following which the simple catheter is removed and replaced with the dilatation catheter, as previously described. The through lumen also permits materials to be injected into the vessel 10 at the distal tip of the catheter. This is done through the injection port 58 of fitting 28. These materials may be radiographic contrast agents, fibrinolytic substances, or medicines. The through lumen also allows pressures at the distal end of the catheter or balloon to be monitored proximally.

The outer catheter 14 and the inner catheter 26 are made of a plastic material that is flexible but non-collapsing under pressure. The balloon 24 is made of a flexible essentially non-elastomeric material, such as polyethylene. The inner catheter 26 and balloon 24 may be constructed in a single piece, or they may be separate pieces joined together by adhesive or adhesive and suture winding.

What is claimed is:

1. A dilatation catheter comprising an elongated flexible tubular outer catheter, a housing having axially aligned distal and proximal openings, said outer catheter having its proximal end attached to said housing in alignment with the distal opening thereof, a dilatation balloon having its distal end in secured relationship to the distal end of said outer catheter, an elongated flexible tubular inner catheter extending along said outer catheter in generally spaced relation thereto and through said housing and the distal and proximal openings thereof, said inner catheter having its distal end attached in sealed communicating relation with the proximal end of said balloon to provide a passage through the balloon, means associated with the proximal opening of said housing to grip the proximal end of said inner catheter when the same has been tensioned to remove the slack from said balloon and inner catheter, said means being selectively operable to grip and ungrip said inner catheter and having an open-ended unobstructed rectilinear throughbore axially aligned with said axially aligned distal and proximal openings to thereby provide said catheter with a permanently open central lumen whereby said dilatation catheter may be readily guided for emplacement by a pre-positioned guide wire, and a radially enlarged chamber defined within the housing between said distal and proximal openings to receive and store a layup loop of said inner catheter when the proximal end thereof is manually fed inwardly of said proximal opening of said housing between successive ungripping and gripping operations of said means to thereby condition said balloon for eversion from said outer catheter.

2. The catheter of claim 1, said means comprising an adjustable O-ring gripping and sealing means, said housing having an inflation fluid port whereby liquid may be introduced into said housing and between said catheters to effect eversion movement of said balloon and subsequent lateral expansion thereof.

3. The catheter of claim 2, said outer catheter having a tubular wall, said tubular wall having defined therein a purge lumen, a purge fluid port, separate and apart from said inflation fluid port, in communication with the proximal end of said purge lumen, the distal end of said purge lumen being in communication with the distal end of an intracatheter's lumen, and separate control valves for said ports to selectively open and close said valves.

* * * * *